US007476867B2

(12) United States Patent
Fritsch et al.

(10) Patent No.: US 7,476,867 B2
(45) Date of Patent: Jan. 13, 2009

(54) DEVICE AND METHOD FOR QUALITY ASSURANCE AND ONLINE VERIFICATION OF RADIATION THERAPY

(75) Inventors: Ernst Fritsch, Leutershausen (DE); Friedrich Friedl, Burgthann (DE); Igor Gomola, Nuremberg (DE); Cristiana Peroni, Pino Torinese (IT); Marchetto Flavio, Borgaro Torinese (IT); Marco Donetti, Turin (IT); Roberto Cirio, Turin (IT)

(73) Assignee: IBA, Louvain-La-Neuve (BE)

( * ) Notice: Subject to any disclaimer, the term of this patent is extended or adjusted under 35 U.S.C. 154(b) by 17 days.

(21) Appl. No.: 11/440,890

(22) Filed: May 25, 2006

(65) Prior Publication Data

US 2006/0266951 A1    Nov. 30, 2006

Related U.S. Application Data

(60) Provisional application No. 60/685,712, filed on May 27, 2005.

(51) Int. Cl.
*G01T 1/18* (2006.01)
*H01J 47/00* (2006.01)

(52) U.S. Cl. .................................................. 250/385.1
(58) Field of Classification Search .............. 250/385.1, 250/385.2, 335, 389, 374; 378/97
See application file for complete search history.

(56) References Cited

U.S. PATENT DOCUMENTS

| | | | | |
|---|---|---|---|---|
| 4,075,527 A * | 2/1978 | Cummings | | 313/93 |
| 4,686,369 A * | 8/1987 | McDaniel et al. | | 250/385.1 |
| 5,162,450 A * | 11/1992 | Chao et al. | | 525/396 |
| 5,631,470 A * | 5/1997 | Day et al. | | 250/385.1 |
| 5,742,061 A * | 4/1998 | Lemonnier et al. | | 250/385.1 |
| 6,236,711 B1 | 5/2001 | Lumma | | |
| 6,545,422 B1 * | 4/2003 | George et al. | | 315/169.3 |
| 2002/0149305 A1 * | 10/2002 | Danielsson et al. | | 313/105 CM |
| 2005/0173648 A1 * | 8/2005 | Schmidt et al. | | 250/374 |

OTHER PUBLICATIONS

Bonin et al., "A pixel chamber to monitor the beam performances in hadron therapy", Elsevier, Nuclear Instruments and Methods in Physics Research A 519 (2004), 674-686.*
IRF6644 datasheet, www.irf.com.*
Bonin et al., A Pixel Chamber to Monitor The Beam Performances in Handrontherapy, Elsevier Prepring, Dec. 9, 2003, pp. 1-22.
S. Amerio et al., "Dosimetric Characterization of a Large Area Pixel-Segmented Ionization Chamber", Med. Physics, Feb. 2004, pp. 414-420, vol. 31, (2), AIP, Melville, New York, US.
C. N. De Souza et al., "Two New Parallel-Plate Ionization Chambers for Electron Beam Dosimetry", Radiation Measurements, Jan. 1996, pp. 65-74, vol. 26, (1), Elsevier Science Ltd., Amsterdam, NL.

(Continued)

*Primary Examiner*—David P Porta
*Assistant Examiner*—Kiho Kim
(74) *Attorney, Agent, or Firm*—Norris McLaughlin & Marcus

(57) ABSTRACT

A radiation monitor and method of monitoring the radiation delivered to a target by a radiation device is described. The radiation monitor contains a set or matrix of pixel ion chambers. The pixel ion chambers are preferably constructed of a top electrode and a segmented electrode connected to the top electrode through a mid layer. The plurality of pixel ion chambers is formed within the mid layer extending from the top electrode to the segmented electrode. The mid layer is laminated to the top electrode and segmented electrode by an array of adhesive dots, wherein the adhesive dots are dimensioned and positioned on the mid layer to provide ventilation slits or channels for the ion chambers.

11 Claims, 4 Drawing Sheets

OTHER PUBLICATIONS

J. Pardo et al., "Development and Operation of a Pixel Segmented Liquid-Filled Linear Array for Radiotherapy Quality Assurance", Physics in Medicine and Biology, Apr. 21, 2005, pp. 1703-1716, vol. 50, (8), Institute of Physics Publishing, Bristol, GB.

* cited by examiner

DEVICE AND METHOD FOR QUALITY ASSURANCE AND ONLINE VERIFICATION OF RADIATION THERAPY

CROSS REFERENCE TO RELATED APPLICATION

This application claims the benefit of U.S. Provisional Patent Application No. 60/685,712, filed May 27, 2005, the entirety of which is hereby incorporated by reference into this application.

FIELD OF THE INVENTION

The present invention is related to a device and method for quality assurance and online verification of a radiation therapy apparatus such as an IMRT apparatus.

STATE OF THE ART

When delivering radiotherapy to a patient, it is of the utmost importance to ensure that the prescribed dose is delivered to the target volume.

Radiographic X-ray film has been used extensively for performing quality assurance of radiation therapy apparatuses. A thin plastic film with a radiation sensitive emulsion (e.g. silver bromide, AgBr grains suspended in gelatin) is irradiated, and ionization of AgBr grains forms an image, after development. Optical density must be measured using a densitomer. This process is time consuming, and cannot be performed in real-time.

A pixel chamber is known from Bonin et al: "A pixel chamber to monitor the beam performances in hadron therapy," Nuclear Instruments and Methods in Physics Research A 519 (2004) 674-686. This document discloses a matrix of ionization chambers. This device comprises a set of successive ionization chambers. The general principle of an ionization chamber is as follows: A high voltage is applied between two parallel electrodes. A gas (here air or nitrogen) between the plates is ionized by the beam passing perpendicularly to the planes. As a result of the electric field, the ions are collected on the electrodes, and the charge can be measured. As the creation of one electron-ion pair requires a known average energy, depending on the gas and on the irradiation type, the collected charge is directly proportional to the energy deposited in the gas. The charge is measured by means of a recycling integrator circuit providing a 16-bit counter value proportional to the detected charge. The recycling integrator was developed as a 0.8 µm CMOS technology chip (TERA06) by INFN (Instituto Nazionale di Fisica Nucleare, Torino). Each of these chips provides 64 channels. The minimum detectable charge is adjustable between 50 fC and 800 fC, and the counting rate in the linear region can be as high as 5 MHz. The values provided by the counters are sent to an Ionization Chamber Electronic Unit (ICEU) and the processed data are used by the Master Control Unit (MCU) of the irradiation apparatus for performing the control, safety and operator interface functions. A redundant pad chamber performs a redundant check, for improving safety.

As described above, the monitor comprises two strip planes. In addition to these strip planes, the monitor may comprise an integral plane, measuring the instantaneous beam current, and hence the total instantaneous dose. This data is acquired at the same rate as the strip data. The monitor also comprises a plane made of individual square pads. The pads have a size of 0.7 cm×0.7 cm. A matrix of 32×32 conductive pixels on one side, and tracks (one for each pixel) on the other side of the PCB is provided.

However, this known pixel ionization chamber presents some disadvantages. One disadvantage is the presence of mechanical instability. The distance between successive planes is defined by an external frame. Mechanical deformation or microphonic effect can affect the distance between electrodes in a significant way, thereby negatively affecting the accuracy and precision of the date. Another disadvantage with the known systems is the transparency. The significant amount of copper produces backscattering, and reduces transparency, thereby reducing the applicability of this device as a transmission chamber.

What is needed is a device and method for quality assurance and on-line monitoring of the fluency rate produced by a radiotherapy device that minimizes or eliminates the problems in the prior art. What is need is a more accurate method and device for determining the corresponding dose deposited in a target volume.

SUMMARY OF THE INVENTION

A radiation monitor and method of monitoring the radiation delivered to a target by a radiation device is described. The radiation monitor contains a set or matrix of pixel ion chambers. The pixel ion chambers are preferably constructed of a top electrode and a segmented electrode connected to the top electrode through a mid layer. The plurality of pixel ion chambers is formed within the mid layer extending from the top electrode to the segmented electrode. The mid layer is laminated to the top electrode and segmented electrode by an array of adhesive dots, wherein the adhesive dots are dimensioned and positioned on the mid layer to provide ventilation slits or channels for the ion chambers.

In one embodiment a pixel ion chamber with reduced leakage is described. The pixel ion chamber contains a top electrode, a mid layer connected to the top electrode, and a segmented electrode connected to the mid layer. The mid layer has a hole extending through the width of mid layer forming a chamber. The segmented electrode has a top layer of a carbon print pixel that interfaces the corresponding chamber of the mid layer. A copper guard ring encircles the pixel providing guarding from leakage. Preferably the pixel ion chamber also has a signal track connected to the pixel by a plugged via, thereby forming a pixel signal track, and a copper guard track surrounding each individual pixel signal track for further guarding from leakage. For additional protection from leakage, the mid layer is laminated to the top electrode and segmented electrode by adhesive dots. The adhesive dots are dimensioned and positioned on the mid layer to provide ventilation channels for the chambers.

In another embodiment, a monitor with improved transparency for measuring radiation is described. The monitor is constructed with lower Z material and as a result, a more transparent chamber is obtained. The monitor has a matrix of pixel ion chambers. The pixel ion chambers are comprised of a top electrode, a mid layer, and a segmented electrode. The top electrode has a top outer layer of printed carbon as an EMC protection shield. The pixel ion chamber of may also have a printed circuit board constructed of material free of bromide or other high atomic number compounds.

In another embodiment, a method of monitoring the radiation delivered to a target by a radiation device is described. Any of the radiation monitors provided by the current invention are positioned between the radiation device and the target so that the radiation beam travels through the monitor prior to delivering the radiation to the target. The radiation is then delivered to the target. The fluency rate produced by a radiation device is measured in real-time by the monitor. The target can be a patient receiving radiation treatment. The dose the patient is receiving in real time can be determined from the measured radiation and compared to a target treatment dose.

DETAILED DESCRIPTION OF THE INVENTION

A monitoring device for measuring radiation in real time is described. The monitoring device can be used for monitoring the fluency rate produced by a radiation device. In operation the monitoring device is positioned between the radiation device and the target, such as a patient receiving radiation treatment. In such a position, the device measures the fluency rate and the corresponding radiation dose can be determined in real time. The following description is of the preferred embodiment of the present invention.

Figure 1:
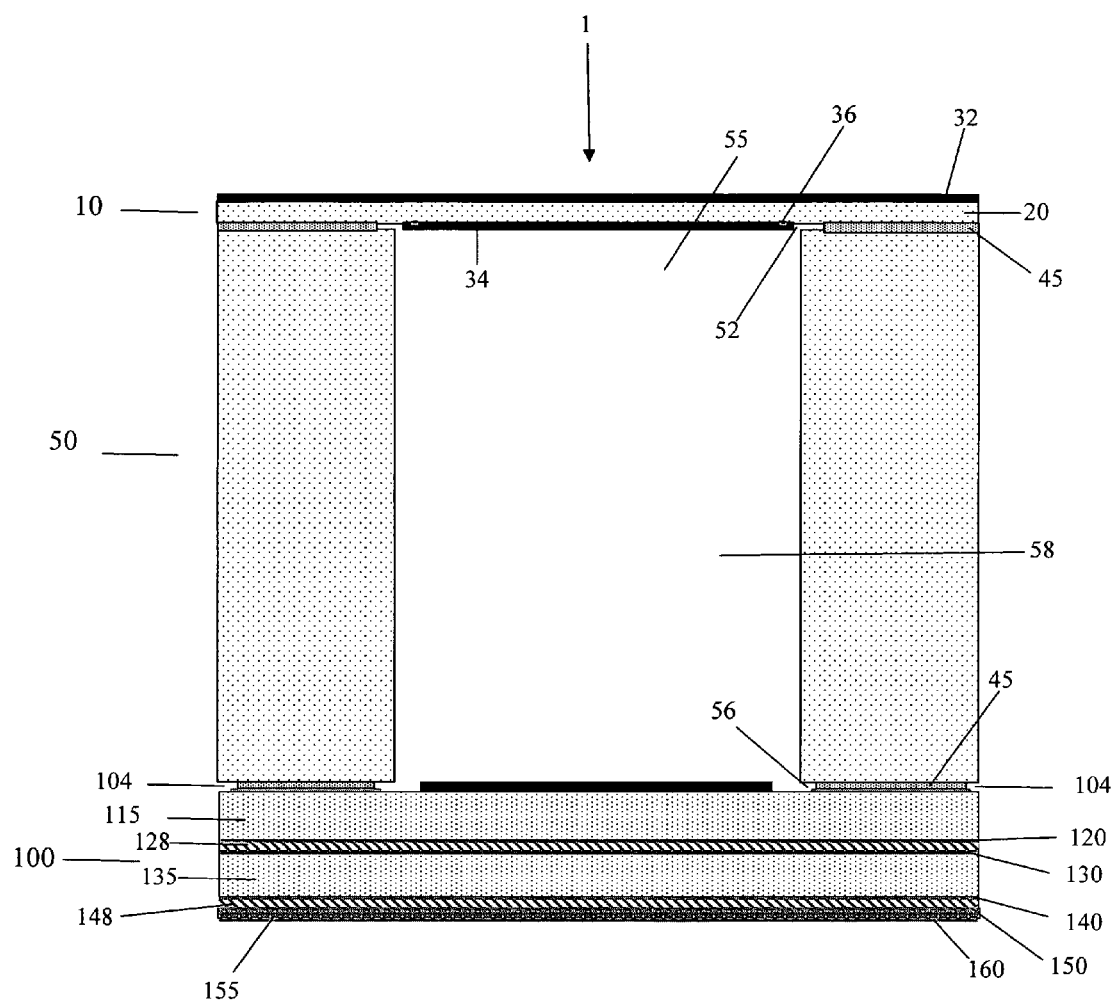
FIG. 1 provides a side view of the layer stack of the pixel ion chamber 1 of the present invention.

The monitoring device is made up of an array or matrix of pixel ion chambers. FIG. 1 shows the side view of the structure of a single pixel ion chamber 1 constructed in accordance with the present invention. The pixel ion chamber 1 has a top electrode 10, a mid layer 50, and a segmented electrode 100.

The top electrode 10 has a polyimide layer 20 sandwiched on both sides by carbon layers 32 and 34. The top electrode could be made from any material, depending on the application such as, for example another plastic material, graphite, or metal. Preferably the polyimide is about 50 μm thick and is constructed from Pyralux AP 8525R®. Preferably the carbon layers are printed carbon of about 25 μm thick.

Figure 2:
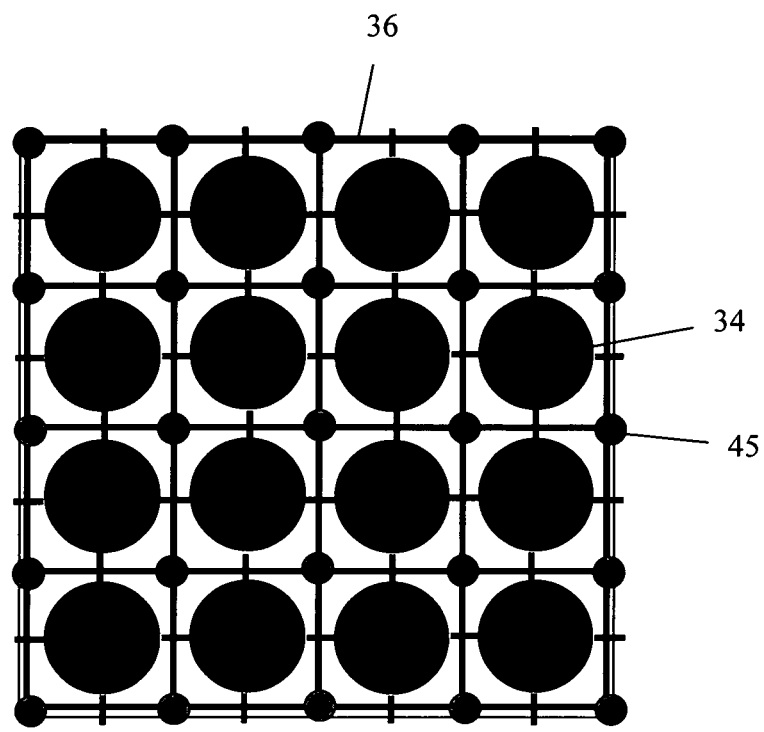
FIG. 2 provides a top view of the inner carbon layer 34 of the top electrode 10 of an array or matrix of pixel ion chambers.

The outer carbon layer 32 of the top electrode 10 acts as an Electro-Magnetic Compatibility ("EMC") shield. The outer carbon layer 32 generally extends across the entire plane of the pixel ion chamber 1. The inner carbon layer 34 is structured according to hole 55 of mid layer 50 and dimensioned so that the circumference of the inner carbon layer fits into and is smaller than the circumference of the hole 55. Preferably, the inner carbon layer 34, and hole 55 are substantially circular in shape, (although they could be any shape depending on the application and easy manufacturing) and differ in diameter (with the inner carbon layer 34 being the smaller diameter). In the preferred embodiment the inner carbon layer is about 4.4 mm diameter, and the corresponding hole 55 in mid layer 50 has a diameter of about 4.5 mm. This arrangement assures that the mid layer 50 does not come in contact with the center electrodes 34 and 105. A matrix of printed carbon layer 34 are connected to each other by means of a copper grid 36 (as illustrated in FIG. 2) to assure a good and uniform conductivity.

The mid layer 50 is constructed of pure polycarbonate plate. Preferably the mid layer 50 is about 5 mm thick, but can larger or smaller depending on the diameter of the chamber. In the approximate center of mid layer 50, a hole 55 extends through the entire thickness of the mid layer 50. The hole 58 is preferably about 4.5 mm in diameter and extends substantially perpendicular to the horizontal plane of mid layer 50 to form a cylinder.

The top end 52 of mid layer 50 is laminated to the polyimide layer 20 of top electrode 10 by means of an adhesive 45. Preferably the adhesive is in the form of adhesive dots 45 that are about 100 μm thick. The adhesive material is preferably epoxy with a diameter from about 1 to 2 mm. The bottom end 56 of mid layer 50 is likewise laminated to the top layer 105 of the segmented electrode 100 by an adhesive 45, which is preferably in the form of adhesive dots 45. Once the mid layer 50 is adhered to the top 20 and segmented electrode 100, chamber 58 is formed in the hole 55 of mid layer 50.

The adhesive or glue dots 45 perform several functions in addition to adhering the mid layer 50 to the top electrode 10 and to the segmented electrode 100. First the shape and position of the dots 45 is such that it does not entirely seal the chamber 58, but instead provides ventilation slits or open channels on both sides of the mid layer 50 for the chamber 58. The glue dots 45 are positioned around the inner carbon layer 34 of the top electrode, and around the pixels 105 of the segmented electrode 100. In absolute Dosimetry vented chambers are preferable to sealed chamber, because sealed chambers tend to not to be, or remain, gas tight, which leads to an unpredictable change in sensitivity.

Figure 3:
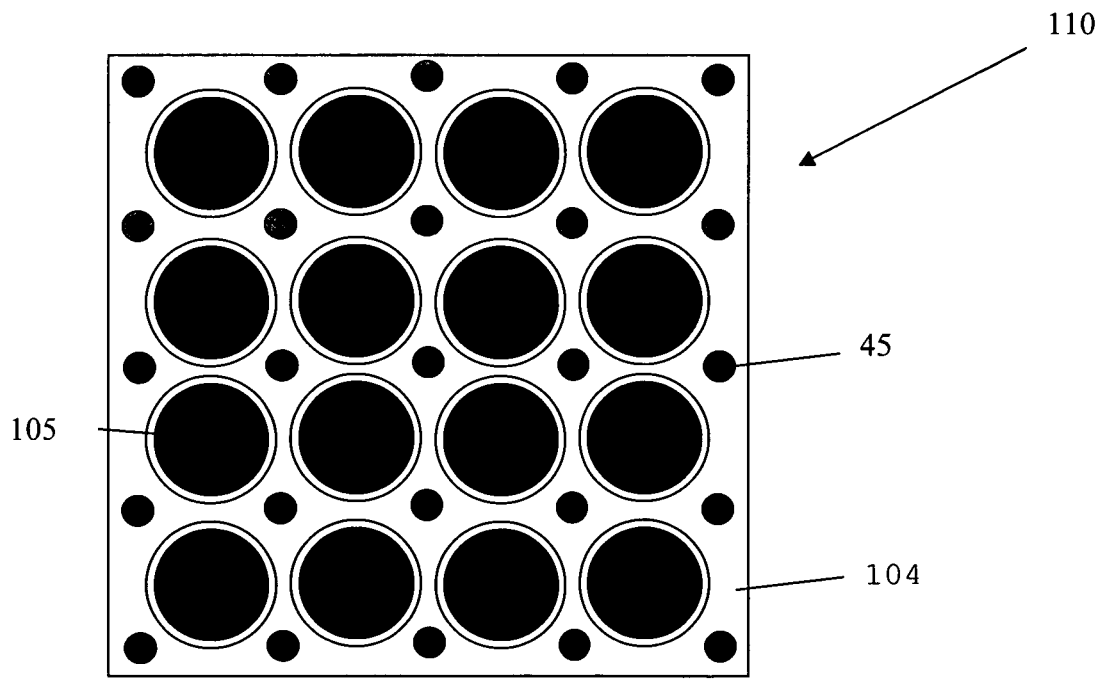
FIG. 3 provides a top view of the first layer 110 of the segmented electrode 100 of an array or matrix of pixel ion chambers.

Additionally, the use of a grid of glue dots 45, as illustrated in FIGS. 2 and 3 (which provides the top view of the cell-supporting structure of an array or matrix of pixel ion chambers 1), permits the construction without the use of an external mechanical frame. The elimination of such a frame from the pixel ion chamber array minimizes or eliminates mechanical deformation or microphonic effect that is present when an external frame is used. In this way, the accuracy of the measurements obtained increases over devices that utilize external frames.

The glue dots 45 also assist in minimizing or eliminating mid layer 50 leakage that can occur between the top electrode 10 through the mid layer 50 to the segmented electrode 100. Such leakage disturbs the measurements and its reduction or elimination also increases the accuracy of the measurement. The glue dots act as spacers that prevent the mid layer 50 from touching the collecting electrodes, which is one technique of the present invention to reduce leakage. As discussed below, the present invention provides other techniques that may be used alone, or in combination with the use of glue dots, to reduce leakage.

Figure 4:
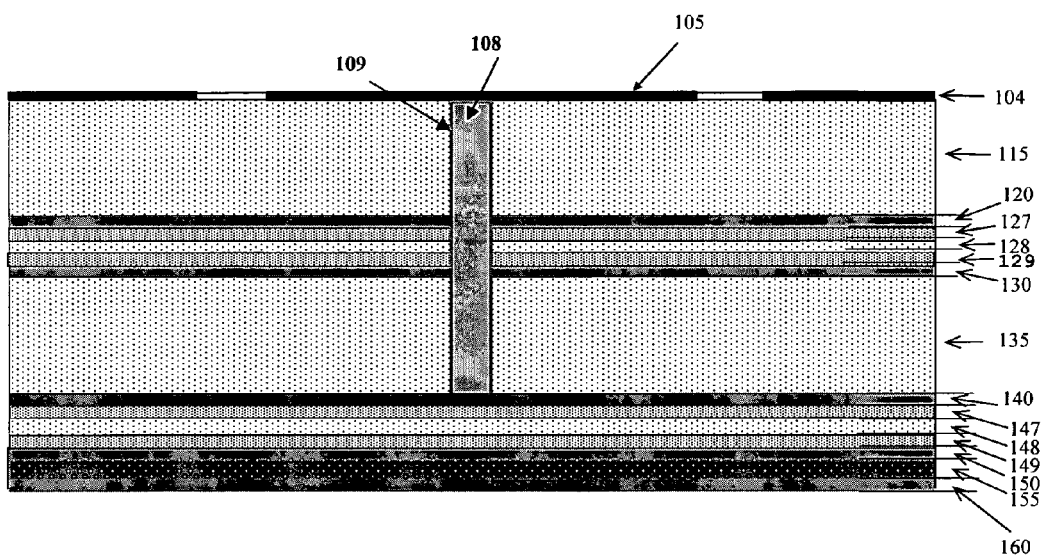
FIG. 4 provides a detailed side view of the segmented electrode 110.

The detailed side view of the segmented electrode is illustrated in FIG. 4 (not drawn to scale). In the preferred embodiment, the segmented electrode 100 comprises a six layer printed circuit board. The first layer 110, facing the inside of the chamber 58, is comprised of a pixel 105 constructed preferably of carbon print, or alternatively graphite or thin metal. The pixels 105 are preferably about 25 μm thick. The pixel 105 is shaped and dimensioned according to the shape and dimension of the hole 55 so that the pixel 105 fits into the hole 55. Preferably, the pixel 105 is substantially circular (although they could be any shape depending on the application and easy manufacturing) with a diameter less than the diameter of the hole 55. In the preferred embodiment, the pixel 105 is about 0.4 mm smaller in diameter than the diameter of the hole 55 in mid layer 50. More preferably, the hole 55 has a diameter of about 4.5 mm and the pixel 105 has a diameter of about 4.1 mm.

Figure 5:
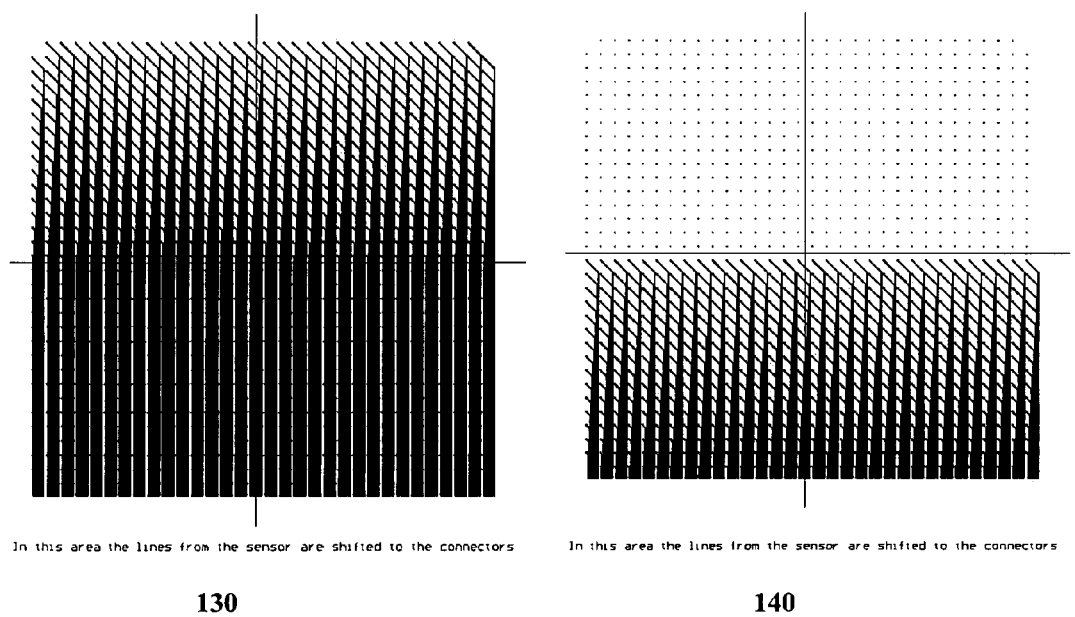
FIG. 5 provides an illustration of the structure of the signal layers 3 and 4 130 and 140.

The pixel 105 is connected to the signal tracks, shown in FIG. 5, by a plugged via 108. The plugged via 108 is a vertical interconnection between two insulation layers 115 and 135.

Via 108 is preferably constructed of a copper cylinder 109 of a thickness of about 20 μm created in a galvanic process. The via 108 provides the vertical interconnection through the insulation layers and connects the pixels 105 to the signal tracks.

Directly beneath the first layer 110 is a layer of Core material 115 sandwiched by two copper guard tracks 104 and 120. Preferably, the layer 115 is constructed of pure polyimide, or alternatively glass fiber reinforced Duraver® 156 material, or any low Z PCB material and is about 1000 μm thick. This thickness permits Core material to absorb back scattered electrons. These copper tracks are preferably about 18 μm thick (unless otherwise noted all copper tracks or layers are preferably about 18 μm thick). The top copper guard track 104, which in combination with the pixel 105 provides the first layer 110 of the segmented electrode 100. The top copper guard track 104 is shaped to surround the pixel 105, thereby preventing leakage from the top electrode 10. The top copper guard track 104 has holes that correspond to the shape of the pixels 105, but have a larger diameter so it does not overlap the pixels 105. The preferred configuration of the top view of the first layer 110 is illustrated in FIG. 3. In the preferred embodiment, the diameter of the holes in the top copper guard track 104 is about 4.9 mm. This results in an average copper density of around 60% for the top copper guard track 104. Adhesive dots 45 are also used to connect the first layer 110 of the segmented electrode 100 to the mid layer 50.

The second layer is comprised of the bottom copper guard track 120 and is positioned on the opposite side of the Core material 115 from that of the top copper guard track 104. The bottom copper guard track 120 prevents cross-talk between the signal tracks (not shown) and the pixels 105. The guard 120 is connected to a potential of low impedance (not shown) that is very close to the sensor input potential (±1 mV). The average copper density of the bottom copper guard track 120 is about 100%, except that the track does not extend through the plugged via 108.

Sandwiched between the second layer 120 and the third layer 130 is an insulation layer 128, preferably constructed from about a 50 μm thick of Polyimide (Pyralux® AP 8525R). Adhesive layers 127 and 129 on each side of the insulation layer 128 of about 25 μm thick are provided.

The third and fourth layers and are copper layers 130 and 140 of about 18 μm on either side another layer of Core material 135 (preferably glass fiber reinforced Duraver® 156 material) of about a 1000 μm thick. Both the third and fourth layers 130 and 140 operate as guard tracks and surround the pixel signal tracks connecting the pixels 105 to the read out electronics (not shown) on one side of the pixel chamber 1. To reduce leakage, the pixel track, which is comprised of the electrodes and the copper track to the readout electronics, is also surrounded by copper guard tracks (not shown). Preferably the pixel track is surrounded on both sides, as well as on the top by the third layer 130 and the bottom by the fourth layer 140. The average copper density will preferably be around 50% for the third and fourth layer 130 and 140. FIG. 5 illustrates the structure of the signal for layers 3 and 4, 130 and 140.

Sandwiched between the fourth layer 140 and the fifth layer 150 is another insulation layer 148, preferably constructed from about a 50 μm thick of Polyimide, such as for example Pyralux® AP 8525R. Adhesive layers 147 and 149 on each side of the insulation layer 148 of about 25 μm thick are provided.

The fifth and sixth layers 150 and 160 comprise unstructured copper layers of about 18 μm. Sandwiched between the fifth and sixth layers 150 and 160 is a 50 μm thick polyimide foil 155, such as for example Pyralux® AP 8525R. Layer 5 150 is connected to the guard potential (not shown) and layer 6 160 is connected to a protective ground (not shown) in order to improve the electromagnetic immunity. The average copper density is preferably about 100% for both layers 150 and 160.

In a further embodiment an array of pixel ion chambers is constructed as illustrated in FIGS. 2 and 3. Use of the glue dots between layers according the invention provides a cell-supporting structure, without a frame. Use of printed carbon electrodes instead of copper, providing a lower Z material, a more transparent chamber is obtained. Further transparency is obtained use of bromide free PCB material (low Z material). Additionally, the use of a printed carbon layer on top of the top electrode acts as an electromagnetic shield. Finally, the copper tracks as guard layers provide protection from and minimize leakage.

In a further embodiment, the chamber array as provided by the current invention is incorporated into an online monitor for measuring, in real-time, the radiation fluency rate produced by a radiotherapy device. Among the uses for an online monitor of the present invention, is the monitoring of dose delivery of radiation to a patient receiving radiation therapy, and provide dose verification in real-time. In this embodiment, the monitor with chamber array can be positioned between the radiation device and the target; in the case of radiation therapy the target is the patient, because of the improved transparency of the chamber array, a direct measurement of the fluency can be obtained thereby eliminating the need to calculate the dose delivered to the patient by indirect measurements and calculations.

There will be various modifications, adjustments, and applications of the disclosed invention that will be apparent to those of skill in the art, and the present application is intended to cover such embodiments. Although the present invention has been described in the context of certain preferred embodiments, it is intended that the full scope of these be measured by reference to the scope of the following claims.

The disclosures of various publications, patents and patent applications that are cited herein are incorporated by reference in their entireties.

The invention claimed is:

1. A radiation monitor comprising:
    a set of pixel ion chambers wherein the pixel ion chambers comprise
    a top electrode;
    a segmented electrode connected to the top electrode through a mid layer; and
    a plurality of chambers formed within the mid layer extending from the top electrodes to the segmented electrodes;
    wherein the mid layer is laminated to the top electrodes and segmented electrodes by an array of adhesive dots, wherein the adhesive dots are dimensioned and positioned on the mid layer to provide ventilation slits or channels for the pixel ion chambers, and wherein the top electrodes comprise an inner printed carbon layer wherein the inner carbon layers are connected by a copper grid.

2. The radiation monitor of claim 1 wherein the adhesive dots are formed from epoxy and have a diameter of about 1 to 2 mm.

3. A pixel ion chamber with reduced leakage comprising:
    a top electrode;
    a mid layer connected to the top electrode, wherein the mid layer has hole extending through forming a chamber;

a segmented electrode connected to the mid layer; wherein the segmented electrode comprises a top layer of a carbon print pixel that interfaces the corresponding chamber of the mid layer, and;

a copper guard ring encircling the pixel;

a signal track connected to the pixel by a plugged via, thereby forming a pixel track; and a copper guard track surrounding the pixel tracks.

4. The pixel ion chamber of claim 3 wherein the mid layer is laminated to the top electrode and segmented electrode by adhesive dots, wherein the adhesive dots are dimensioned and positioned on the mid layer to provide ventilation channels for the chambers.

5. A monitor comprising a matrix of pixel ion chambers constructed in accordance with claim 4.

6. A monitor with improved transparency for measuring radiation comprising:

a matrix of pixel ion chambers, wherein the pixel ion chambers comprise:

a top electrode;

a mid layer;

a segmented electrode;

a signal track connected to the pixel by plugged via to form a pixel track; and copper guard tracks surrounding the pixel tracks, wherein the top electrode comprises a top outer layer of printed carbon as an EMC shield.

7. The monitor of claim 6 wherein the pixel ion chambers further comprise a printed circuit board constructed of bromide free material.

8. The monitor of claim 7 where the pixel ion chambers wherein the mid layer is laminated to the top electrodes and segmented electrodes by an array of adhesive dots, wherein the adhesive dots are dimensioned and positioned on the mid layer to provide ventilation slits or channels for the pixel ion chambers.

9. A method of monitoring the radiation delivered to a target by a radiation device comprising:

positioning the radiation monitor of any of claims 5 or 6 between the radiation device and the target so that the radiation beam travels through the monitor prior to delivering the radiation to the target;

delivering the radiation to the target; and measuring the fluency rate produced by a radiation device.

10. The method of claim 9 wherein the target is a patient receiving radiation treatment.

11. The method of claim 10 further comprising the step of determining the dose the patient is receiving in real time from the measured radiation and comparing the dose to a target treatment dose.

* * * * *